(12) United States Patent
Besins et al.

(10) Patent No.: US 7,829,115 B2
(45) Date of Patent: Nov. 9, 2010

(54) PHARMACEUTICAL COMPOSITION BASED ON MICRONIZED PROGESTERONE, PREPARATION METHOD AND USES THEREOF

(75) Inventors: Antoine Besins, Brussels (BE); Jerome Besse, Listrac Medoc (FR)

(73) Assignee: Besins Manufacturing Belgium, Brussels (BE)

( * ) Notice: Subject to any disclaimer, the term of this patent is extended or adjusted under 35 U.S.C. 154(b) by 104 days.

(21) Appl. No.: 12/071,822

(22) Filed: Feb. 27, 2008

(65) Prior Publication Data

US 2009/0123534 A1   May 14, 2009

Related U.S. Application Data

(63) Continuation of application No. 10/495,242, filed as application No. PCT/FR02/03879 on Nov. 13, 2002, now Pat. No. 7,431,941.

(30) Foreign Application Priority Data

Nov. 13, 2001   (FR)   .................. 01 14653

(51) Int. Cl.
*A61K 9/46* (2006.01)
(52) U.S. Cl. .................................... 424/456
(58) Field of Classification Search ........ None
See application file for complete search history.

(56) References Cited

U.S. PATENT DOCUMENTS

| | | | |
|---|---|---|---|
| 4,196,188 | A | 4/1980 | Besins |
| 5,140,021 | A | 8/1992 | Maxson et al. |
| 6,077,531 | A | 6/2000 | Salin-Drouin |
| 6,165,491 | A | 12/2000 | Grasset et al. |
| 7,431,941 | B2 | 10/2008 | Besins et al. |
| 2002/0025951 | A1 * | 2/2002 | Kim et al. ............. 514/169 |

FOREIGN PATENT DOCUMENTS

| | | |
|---|---|---|
| EP | 0253607 | 7/1987 |
| EP | 0 598 337 | 5/1994 |
| WO | WO 97/40823 | 11/1997 |

OTHER PUBLICATIONS

Moneret et al.; "Food allergy to peanuts in France—evaluation of 142 observations," Clinical and Experimental Allergy, 1998, vol. 28, pp. 1113-1119.
Dutau et al., "Les Nouveaux Allergenes Alimentaires," Presse Medicale, 09/25/199, vol. 28, No. 28, p. 1553.
Taylor et al., "Peanut Oil is Not Allergenic to Peanut-Sensitive Individuals," J. Allergy Clin. Immunol., 1981, vol. 68, No. 5, pp. 372-375.
Moneret-Vautrin et al., "Risks or Milk Formulas Containing Peanut Oil Contaminated with Peanut Allergens in Infants with Atopic Dermatitis," Perdiatr. Allergy Immunol, 1994, vol. 5, pp. 184-188.
Sabbah et al., "Etude Experimentale de la Sensibilisation a l'arachide Chez Les Cobayes," Allergie et Immunologie, 1994, vol. 26, No. 10, p. 380.
G de Montis et al., "Sensiibilisation a l'arachide et Preparations Vitaminiques en Solution Huileuse," Arch. Pediatr., 1995, vol. 2, p. 25.
Database WPI—Derwent Publications, XP002207311— JP602581-10A, "Progesterone-Emulsified Intravenous Injection—of Progesterone, Vegetable Oil, Lecithin and Opt. Benzyl-Benzoate," Dec. 20, 1985, Daigo Eiyo Kagaku KK.
Office Action dated Nov. 25, 2005 from U.S. Appl. No. 10/495,242 (10 pgs.).
Office Action dated May 12, 2006 from U.S. Appl. No. 10/495,242 (11 pgs.).
Office Action issued Aug. 1, 2008, by the Examiner in U.S. Appl. No. 10/495,242 (US 7,431,941).
Notice of Allowance issued Jun. 11, 2008, by the Examiner in U.S. Appl. No. 10/495,242 (US 7,431,941).
Office Action issued Dec. 12, 2007, by the Examiner in U.S. Appl. No. 10/495,242 (US 7,431,941).
Office Action issued Apr. 23, 2007, by the Examiner in U.S. Appl. No. 10/495,242 (US 7,431,941).

* cited by examiner

*Primary Examiner*—Robert A Wax
*Assistant Examiner*—Bethany Barham
(74) *Attorney, Agent, or Firm*—Foley & Lardner LLP

(57) ABSTRACT

The present invention relates to a pharmaceutical composition comprising micronized progesterone, soya bean lecithin, and at least one oil selected from the group consisting of sunflower oil, olive oil, sesame seed oil, colza oil, almond oil, to the method for the preparation thereof and to the uses thereof for treating a physiological condition linked to insufficiency of progesterone secretion.

26 Claims, 4 Drawing Sheets

—— GAL 221.01 CAPS START BATCH QB01249020, 10/15/01 10:48:30

---- PF0098 CAPS BATCH 5439. 10/02/01 11:33:35
(UTROGESTAN® CAPSULE)

PHARMACEUTICAL COMPOSITION BASED ON MICRONIZED PROGESTERONE, PREPARATION METHOD AND USES THEREOF

CROSS-REFERENCE TO RELATED APPLICATIONS

This application is a continuation of U.S. application Ser. No. 10/495,242, filed May 6, 2004, now U.S. Pat. No. 7,431,941 which is the U.S. National Stage of PCT/FR02/03879, filed Nov. 13, 2002, the entire contents of which are incorporated herein by reference in its entirety. The application also claims priority to FR 01/14653, filed Nov. 13, 2001.

BACKGROUND

The present invention relates to a pharmaceutical composition containing micronized progesterone, soya bean lecithin, and at least one oil selected from the group consisting of sunflower oil, olive oil, sesame seed oil, colza oil and almond oil. It also relates to pharmaceutical products comprising said pharmaceutical composition.

The invention also relates to the method for manufacturing this pharmaceutical composition, as well as to the uses thereof.

Progesterone is a hormone which is synthesized, in women, essentially by the ovary during the postovulation or luteal phase (more precisely by the cells of the corpus luteum) and, to a lesser degree, by the adrenal glands and the placenta during the second part of pregnancy. Non-endocrine synthesis of progesterone, in particular in neurons, is also possible.

A consequence of insufficiency of progesterone secretion in a woman is a loss of its biological effects: progestative effect, anti-androgen effect (action on the skin) and anti-oestrogen effect (the consequence being hyperoestrogenemia: hot flushes, psychogenic difficulties of the anxious or depressive type, weight gain, etc.). This progesterone insufficiency may lead to functional difficulties and diverse clinical manifestations, in particular:

premenstrual syndromes, menstrual irregularities due to disovulation or anovulation, benign mastopathies, perimenopause and menopause.

However, oral administration of progesterone suffers from a serious handicap due to the poor intestinal absorption and to the intense hepatic metabolism (short plasmatic half-life) of this hormone. Only the vaginal, rectal and intramuscular pathways would, to date, make it possible to maintain blood progesterone level at the physiological level of the luteal phase, for several hours.

The LABORATOIRES BESINS-ISCOVESCO have already proposed a solution in order to improve the quality and intensity of the digestive absorption of natural progesterone, in Patent Application FR 76 36007. Specifically, they have developed a formulation of soft capsules containing micronized progesterone in oily suspension. The synergistic effect of the micronization and the use of molecules containing long-chain fatty acids has made it possible to indisputably increase the bioavailability of progesterone taken orally. This formulation has known a great deal of success worldwide. It is sold in France under the trade mark UTROGESTAN®.

The oil which serves as a basis for the oily suspension in UTROGESTAN® is peanut oil.

Peanut (*Arachis hypogae*) is a leguminous plant, a bushy annual plant with yellow flowers, of the Papilionacea family.

In the last 15 years, peanut allergy has become a considerable allergological problem.

Dutau et al. (La Presse Médicale [Medical Press], vol. 28, p. 1553) observe that the prevalence of peanut allergy has recently been estimated at 1.3% in the general population. The increased use of peanut in food, very often in a masked form, perhaps explains this development.

Early sensitizations have been described in infants who have never consumed peanuts in conventional form, but who were apparently sensitized in utero or via maternal milk, through maternalized milks having contained plant fats (peanut oil) or through medicinal preparations in oily solution.

UTROGESTAN® may be prescribed in many cases of therapeutic indications, including as a supplement to the luteal phase during cycles of in vitro fertilization (IVF), and in the case of a danger of abortion or of prevention of repeat abortion due to luteal insufficiency, up to the 12th week of pregnancy. It is therefore possible, in theory, for a foetus to be exposed to UTROGESTAN® in utero.

To date, while the allergenic effects of peanut are definite, a controversy still exists regarding the ability of peanut oil to engender allergenic reactions. Many publications may be cited on this subject, including: Taylor et al., J. Allergy Clin. Immunol., vol. 68, p. 372 (1981); Moneret-Vautrin et al., Pediatr. Allergy Immunol. vol. 5, p. 184 (1994); Sabbah and Lauret, Allergie et Immunologie, vol. 26, p. 380 (1994); de Montis et al., Arch. Pédiatr., vol. 2. p. 25 (1995)).

Given this fact, the applicant company devoted itself to developing a novel pharmaceutical composition, replacing the peanut oil with other oils which do not have high risks of allergenicity, while at the same time endeavouring to conserve the advantages of the prior formula.

DETAILED DESCRIPTION

Figure 1:
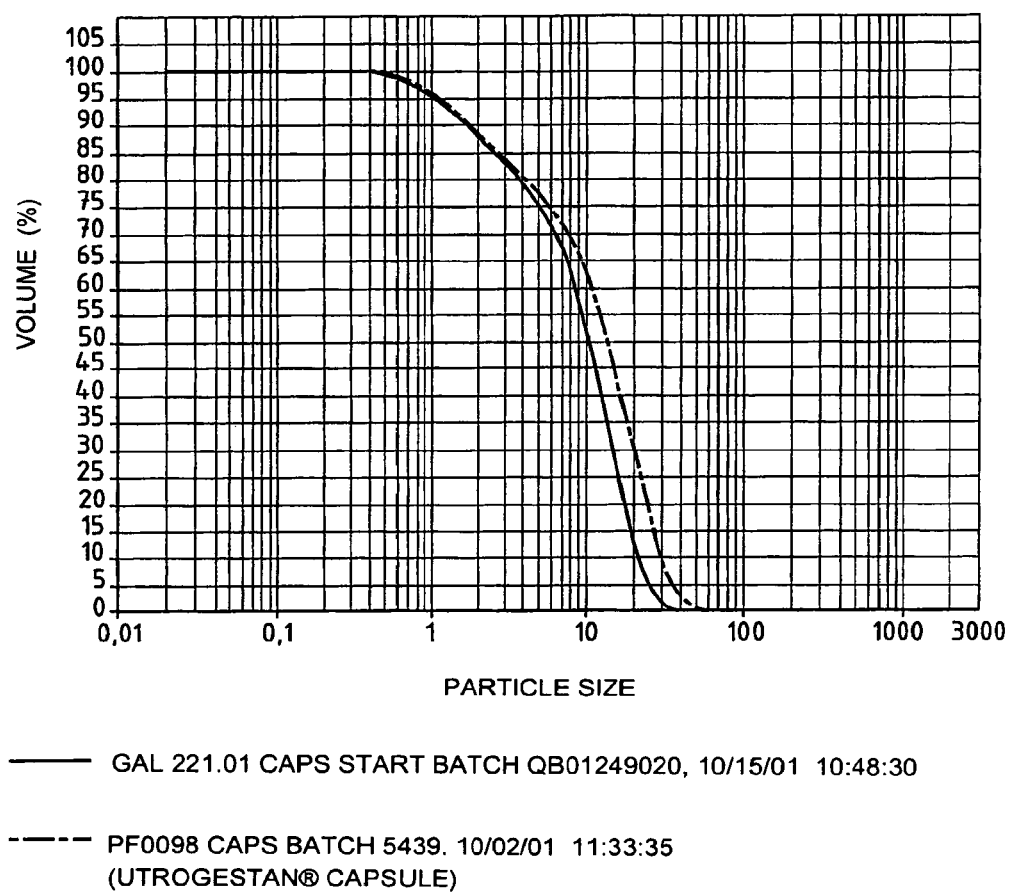
FIG. 1 illustrates the results of a comparative particle size study between UTROGESTAN® capsules (dashed line) and capsules described herein containing sunflower oil (solid line).

After much study and research, during which several plant oils were tested, sunflower oil, olive oil, sesame seed oil, colza oil and almond oil were selected. Specifically, the use of these oils makes it possible to rule out the risks of allergic reactions, while at the same time conserving all of the physicochemical and kinetic characteristics of the prior UTROGESTAN® formulation, characteristics which were the cause of its success. Given that the method manufacturing the prior UTROGESTAN® formulation on an industrial scale comprise steps which are very delicate to carry out, it is to the credit of the applicant company to have succeeded in modifying the formulation without increasing the production difficulties.

In the context of the present invention, the oils can be refined or not. A refined oil is an oil which is obtained from raw oil and which has undergone a set of refining operations. The refined oil is a purified oil having a very low impurity content and especially devoid of highly allergenizing proteins such as gluten.

In the pharmaceutical composition according to the invention, the micronized progesterone is preferably in suspension in sunflower oil, olive oil, sesame seed oil, colza oil, almond oil, or in a mixture of some or all these oils.

The applicant company is aware of U.S. Pat. No. 5,140,021 in the name of GENESIS SYSTEMS CORPORATION (Maxson et al.) which describes a soft capsule containing a micronized progesterone in suspension in a highly unsaturated oil. Sunflower oil appears among the oils cited in this patent. However, the inventors of this patent U.S. Pat. No. 5,140,021 have taken the greatest care to distinguish themselves from the pharmaceutical product UTROGESTAN®, i.e. the formulation developed and currently marketed by the applicant company, based on peanut oil. Thus, the micronized progesterone used in the GENESIS SYSTEMS patent is described as having a particular particle size distribution which is different from that used in UTROGESTAN®.

U.S. Pat. No. 5,140,021 only describes a laboratory scale preparation of the progesterone capsules and provides no teaching regarding the preparation of capsules on an industrial scale. In addition, the progesterone capsules according to said American patent do not contain soya bean lecithin, which is an essential element of the pharmaceutical composition according to the present invention. Specifically, the soya bean lecithin plays the role of an agent for suspending the progesterone particles in the sunflower oil and of a lubricant during encapsulation of the content on an industrial scale.

The invention therefore relates to a pharmaceutical composition comprising micronized progesterone, soya bean lecithin and at least one oil selected from the group consisting of sunflower oil, olive oil, sesame seed oil, colza oil and almond oil.

According to an advantageous embodiment of the pharmaceutical composition according to the invention, the micronized progesterone is in suspension in oil or in a mixture of some or all these oils.

In the context of the present invention, the term "micronized progesterone" is intended to mean a progesterone in which at least 80% of the particles have a particle size of between 1 and 15 µm, preferably 50% of the particles have a particle size of between 1 and 10 µm, and even more preferentially 25% of the particles have a particle size of between 1 and 5 µm, these particle sizes being measured using a laser particle sizer of the Malvern type, by the procedure described in the examples of the present patent application.

During the studies prior to choosing the oil, the applicant company was able to observe, surprisingly and unexpectedly, that the combination of soya bean lecithin with the oils selected according to the invention was very advantageous since it did not modify the particle size of the micronized progesterone in suspension in the oil. In addition, no significant difference in the particle size distribution of the micronized progesterone in suspension became apparent between the composition based on peanut oil and that containing the oils used in accordance with the invention.

With regard to the other oils tested, the particle size was not the same in the presence or absence of the soya bean lecithin. The main advantage of the oils selected according to the invention in physicochemical terms compared to the peanut oil is to simultaneously ensure:

comparable solubilities at saturation of the micronized progesterone;
comparable particle sizes of the suspension;
and comparable in vitro dissolution profiles.

Now, particle size and solubility at saturation significantly influence the in vivo bioavailability of the progesterone.

The choice of these oils therefore makes it possible to have better control of the particle size distribution of the micronized progesterone in the oily suspension, and also the amount of progesterone solubilized in the oil, and therefore to bring together all of the conditions required for maintaining an in vivo bioavailability similar to that obtained with UTROGESTAN®.

According to an advantageous embodiment of the pharmaceutical composition according to the invention, the progesterone/oil(s) ratio is between 0.15/1 and 3/1, preferably between 0.25/1 and 2/1, preferentially between 0.40/1 and 1/1, and even more preferentially is 0.67/1.

According to an advantageous embodiment of the pharmaceutical composition of the invention, the soya bean lecithin/oil(s) ratio is between 0.005/1 and 0.3/1, preferably between 0.01/1 and 0.2/1, preferentially between 0.040/1 and 0.1/1, and even more preferentially is 0.067/1. In other embodiments, the ratio of soya bean lecithin/oil(s) is 0.0067/1.

The pharmaceutical composition according to the invention may also comprise an oestrogen or an ester-type derivative thereof, preferably selected from the group consisting of 17-β-oestradiol, oestrone, 17-α-ethinyl oestradiol and oestradiol valerianate, or phyto-oestrogens and even more preferentially is 17-β-oestradiol.

The pharmaceutical composition according to the invention may be in the form, inter alia, of a soft capsule, of a hard capsule, of a tablet, or a drinkable suspension.

When the pharmaceutical composition according to the invention is integrated into a pharmaceutical product, each dosage unit advantageously comprises between 2 mg and 600 mg of micronized progesterone, preferably between 30 mg and 300 mg, and even more preferentially between 100 mg and 200 mg.

The pharmaceutical composition according to the invention may be administered orally or vaginally, depending on the therapeutic indications.

Vaginal administration also represents an alternative to oral administration in the case of side effects due to the progesterone (drowsiness after oral absorption) or of contraindication to oral administration (hepatopathy).

According to an advantageous embodiment of the pharmaceutical composition according to the invention, the capsule comprises gelatin or an equivalent.

The invention also relates to a method for preparing a pharmaceutical composition comprising micronized progesterone, soya bean lecithin, and at least one oil selected from the group consisting of sunflower oil, olive oil, sesame seed oil, colza oil and almond oil.

This method comprises the following successive steps:
mixing of oil(s) and of soya bean lecithin is carried out, with stirring, in order to obtain a mixture;
the micronized progesterone is added, with stirring, to the mixture thus obtained in order to obtain a homogeneous suspension.

This suspension may be administered as such, in the form of a drinkable suspension, or be presented in the form of soft capsules or hard capsules, but may also be used to impregnate an absorbent support presented in the form of powder.

This absorbent support may be of the maltodextrin and/or derivatives, silica and/or derivatives, cyclodextrin and/or derivatives or cellulose powder and/or derivatives type, or a combination thereof, or any other pharmaceutical raw material which possesses equivalent properties.

The powder thus obtained may then be presented in the form of hard capsules or tablets. The hard capsules or tablets containing the powder may also comprise binding agents, disintegrating agents, diluents and/or lubricants.

The invention also relates to the use of the micronized progesterone, of the soya bean lecithin, and of at least one oil selected from the group consisting of sunflower oil, olive oil, sesame seed oil, colza oil and almond oil in the preparation of a medicinal product for treating a physiological condition linked to insufficiency of progesterone secretion.

As examples of such physiological conditions, mention may be made of: luteal insufficiency, menstrual irregularity, premenstrual syndromes, mastodynia, benign mastopathies, premenopause, sterility due to luteal insufficiency, disorders due to menopause, local contraception, for prevention of repeated abortions in the case of luteal insufficiency, danger of premature birth, acne, alopecia, for prevention of osteoporosis, endometrial cancers and epilepsy.

The invention also relates to the use of the micronized progesterone, of the soya bean lecithin, and of at least one oil selected from the group consisting of sunflower oil, olive oil, sesame seed oil, colza oil and almond oil and also of an oestrogen, in the preparation of a medicinal product for treating a physiological condition linked to insufficiency of progesterone secretion. The oestrogen is preferably selected from the group consisting of 17-β-oestradiol, oestrone, 17-α-ethinyl oestradiol, oestradiol valerianate, or phyto-oestrogens and even more preferentially is 17-β-oestradiol.

The invention will be more clearly understood using the nonlimiting examples described below.

EXAMPLE 1

Pharmaceutical Composition in the Form of a Soft Capsule According to the Invention The content of a soft capsule according to the invention is described in Table I below.

TABLE I

| Compound name | Percentage formula (%) | per unit (mg) | Function | References to standards |
|---|---|---|---|---|
| Active substance | | | | |
| Micronized progesterone | 40.00 | 100.00 | Active substance | Ph. Eur. 3$^{rd}$ ed. |
| Excipients | | | | |
| Oil or mixture of oils according to the invention | 59.60 | 149.00 | Diluent | Ph. Eur. 3$^{rd}$ Ed. |
| Soya bean lecithin | 0.40 | 1.00 | Emulsifier | USP 24, NF 19. p. 2471 |

The applicant company has also prepared 500 mg capsules which are homothetic with the 250 mg capsules described above. Thus, the 500 mg capsules contain 200 mg of micronized progesterone, 2 mg of soya bean lecithin, and as an example, 298 mg of sunflower oil.

EXAMPLE 2

Study of Solubility of Micronized Progesterone in Various Oils

In order to select the optimum oily vehicle to replace the peanut oil, while at the same time conserving the physicochemical properties of the prior formulation, the following plant oils were tested with regard to the solubility of progesterone in these oils:
  peanut oil
  olive oil
  sunflower oil
  sunflower oil with a high oleic acid content
  colza oil
  almond oil
  soya bean oil
  sesame seed oil
  corn oil
Standard solutions were prepared as follows:

| | | |
|---|---|---|
| concentrated solution: | progesterone batch A0098 | 10 mg |
| | oil | qs for 20 ml |
| diluted solution: | concentrated solution | 1 ml |
| | tetrahydrofuran (THF) | 10 ml |
| | acetonitrile | qs for 20 ml |
| magnetic stirring: | 5 minutes. | |

The saturated solutions were then prepared as follows:
The saturated solutions in each oil were maintained for one hour with stirring at room temperature, and were then filtered on a nylon filter syringe with a diameter of 25 mm, at 0.45 μm.
Saturated solutions were diluted 200-fold:

| | |
|---|---|
| saturated solution: | 0.5 ml |
| THF: | 50 ml |
| acetonitrile | qs for 100 ml |

The results are given in Table II below:

TABLE II

| OIL TESTED | CONCENTRATION AT SATURATION (mg/ml) | RELATIVE DIFFERENCE* ON THE CONCENTRATION AT SATURATION (%) |
|---|---|---|
| Peanut oil | 16.77 | — |
| Colza oil | 18.14 | +8.2% |
| Sunflower oil | 17.50 | +4.4% |
| Sunflower oil with a high oleic acid content | 8.29 | −50.6% |
| Olive oil | 17.46 | +4.1% |

TABLE III

| OIL TESTED | CONCENTRATION AT SATURATION (mg/ml) | RELATIVE DIFFERENCE* ON THE CONCENTRATION AT SATURATION (%) |
|---|---|---|
| Peanut oil | 18.80 | — |
| Almond oil | 18.98 | +1.0% |

TABLE III-continued

| OIL TESTED | CONCENTRATION AT SATURATION (mg/ml) | RELATIVE DIFFERENCE* ON THE CONCENTRATION AT SATURATION (%) |
|---|---|---|
| Soya bean oil | 16.19 | −13.9% |
| Sesame seed oil | 19.80 | +5.3% |
| Corn oil | 15.60 | −17.0% |

*Peanut oil = reference oil

The colza oil, sunflower, olive oil, sesame seed oil and almond oil were selected following this study of solubility at saturation.

Among the various suppliers of oils mention may be made, by way of example, of:
for the olive oil: LESSIEUR;
for the sunflower oil: HENRY LAMOTTE.

EXAMPLE 3

Manufacturing of Soft Micronized Progesterone Capsules According to the Invention The manufacturing of soft capsules based on micronized progesterone according to the invention is carried out as follows:

The capsules are prepared according to one of the methods known per se to those skilled in the art.

For a batch of 2 300 000 capsules, each containing 100 mg of progesterone, the following procedure is carried out:

The atmosphere is controlled at 22° C.±3° C. and at a relative humidity of 35%±10%.

The following ingredients are weighed:

| | |
|---|---|
| Progesterone | 230.00 kg |
| Sunflower oil | 342.70 kg |
| Soya bean lecithin | 2.30 kg |

A mixer with a volume of 600 liters is placed under vacuum.

Three quarters of the amount of sunflower oil is introduced under vacuum into this mixer and the soya bean lecithin is added.

The mixer is again placed under vacuum (between 0.7 bar and 0.9 bar), followed by stirring at low speed between 10 rpm and 15 rpm.

The progesterone is added under vacuum, followed by the remaining quarter of sunflower oil, and the temperature is brought to 23° C.±3° C.

Next, vigorous stirring is carried out until homogenization is obtained.

The mixer with vigorous stirring is placed under a pressure up to a maximum of 1 bar.

Continuous sieving using a 500 µm sieve is carried out and the mixture is transferred into a storage container.

The storage containers are placed under vacuum and then stirred at between 2400 and 2000 rpm for 15 minutes. They are again placed under vacuum and restirred for 30 minutes at a speed of between 2000 and 2500 rpm.

The stirring is stopped and the containers are left to stand for 5 minutes under vacuum.

The encapsulation is carried out in a conventional manner known to those skilled in the art.

EXAMPLE 4

Determination of the Particle Size of a Capsule According to the Invention

A comparative particle size study was carried out between UTROGESTRAN® capsules and capsules according to the invention containing sunflower oil.

The material used is as follows:
Mastersizer 2000 laser particle sizer
Hydro 2000 SM measuring cell according to the following method:
Amount of sample per measurement: 1 or 2 drops deposited using a pipette
Medium: filtered saturated sunflower oil. This oil is prepared with magnetic stirring, maintaining the temperature at 37° C., for 1 hour, and then filtered on filter paper.
Refractive index: (oil average) 1.4671
Medium volume: 100 ml
Stirring rate: 1800 rpm
Percentage obscuration: between 10 and 20%
Weighted residual percentage: <3%
Number of measurements per preparation: 2. The measurements begin after the percentage obscuration has been stable for 30 min.

The results given in FIG. 1 hereinafter demonstrate that the particle sizes of the two capsules are highly comparable.

Further studies carried out by the Applicant Company have shown that the size distribution of progesterone in sesame seed oil, olive oil, colza oil or almond oil, is also comparable to that obtained in peanut oil.

EXAMPLE 5

Comparative In Vitro Dissolution Study Between a UTROGESTRAN® Capsule and a Capsule According to the Invention A SOTAX AT7 dissolution machine with rotating baskets was used.

20 mg of exactly weighed progesterone are dissolved in 2 ml of ethanol, in a 200 ml volumetric flask (class A), this is then treated with ultrasound and the volume is made up to the capacity line using the dissolution medium (1% Kleptose).

The control solution is filtered on a fiberglass syringe filter with a porosity of 1 µm.

7 tanks are placed in a waterbath at constant temperature, and then 1000 ml of dissolution medium are transferred into each of the 7 tanks.

1 capsule is placed in 6 tanks, and then the baskets are immersed in the dissolution medium at a distance of 25 Mm±2 Mm between the basket and the bottom of the tank.

The baskets are stirred, and then a control solution is prepared.

At each time interval planned (5, 10, 15, 30, 45, 60, 90, 120, 150, 180, 225, 270, 315 and 360 minutes), the samples are collected and then analysed by UV spectrophotometry (λ: 248 nm).

Figure 2:
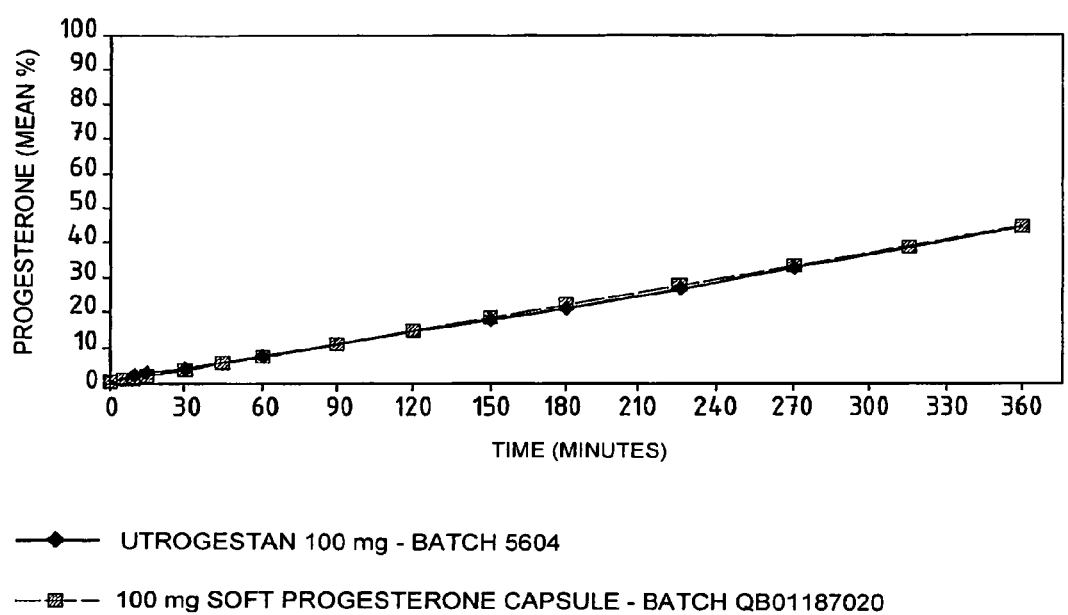
FIG. 2 illustrates the results of a comparative dissolution study between UTROGESTAN® capsules (♦) and capsules described herein containing sunflower oil (■).

The results given in FIG. 2 hereinafter demonstrate that the in vitro dissolution curves for an UTROGESTAN® capsule and for a capsule according to the invention containing sunflower oil are virtually identical.

The physicochemical characteristics of the prior formulation are therefore conserved in the formulation according to the invention.

EXAMPLE 6

Bioequivalence Study Between UTROGESTAN® Capsules and the Pharmaceutical Composition According to the Invention A bioequivalence study was carried out in order to compare capsules according to the invention containing 100 mg progesterone in suspension in sunflower oil with UTROGESTAN® capsules.

The study was carried out on a representative sample of 60 women, in starvation conditions.

Figure 3:
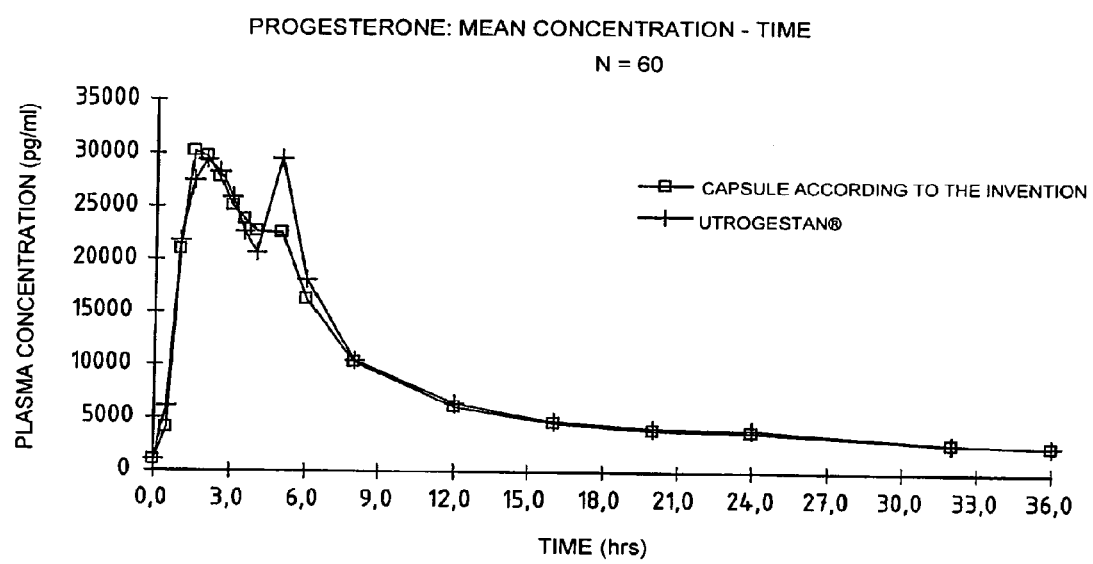
FIG. 3 illustrates the results of a bioequivalence study between UTROGESTAN® capsules (+) and capsules described herein containing sunflower oil (■), with respect to mean plasma concentration (pg/ml).
Figure 4:
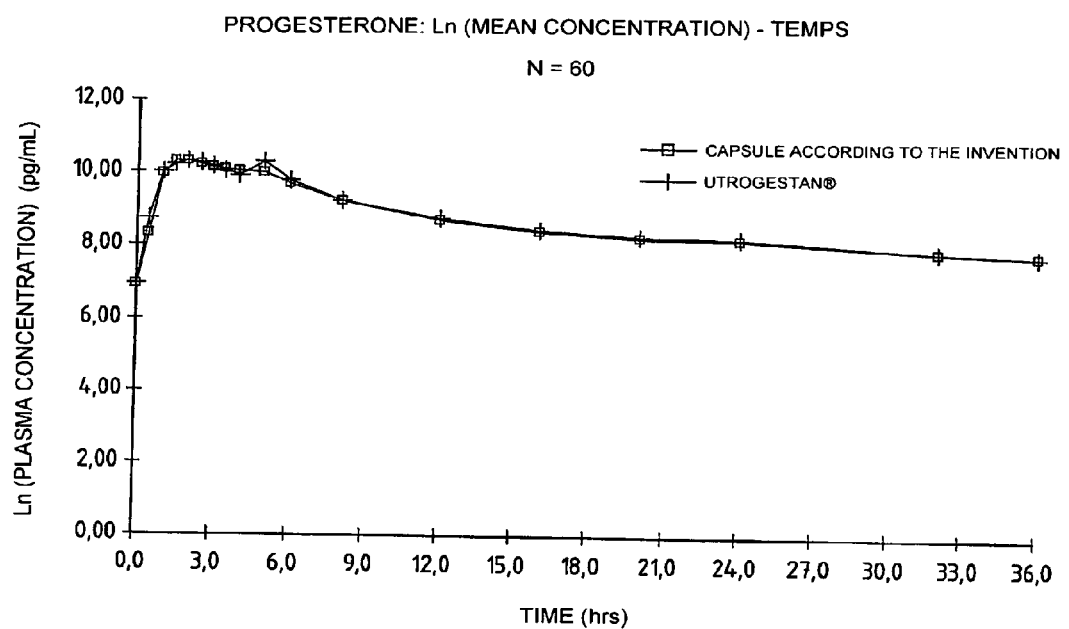
FIG. 4 illustrates the results of a bioequivalence study between UTROGESTAN® capsules (+) and capsules described herein containing sunflower oil (■), with respect to the natural log (Ln) of mean plasma concentration (pg/ml).

The results of the study showed a bioequivalence between the capsules according to the invention and UTROGESTAN® (see FIGS. 3 and 4 thereafter).

The invention claimed is:

1. A pharmaceutical composition comprising: micronized progesterone, soy bean lecithin, and olive oil, wherein at least about 80% of the particles of said micronized progesterone are characterized by a particle size of between 1 and 15 µm, as measured in the composition.

2. The pharmaceutical composition according to claim 1, wherein the progesterone/oil ratio is between 0.15/1 and 3/1.

3. The pharmaceutical composition according to claim 1, wherein the soy bean lecithin/oil ratio is between 0.005/1 and 0.3/1.

4. The pharmaceutical composition according to claim 1, further comprising an oestrogen or an ester-type derivative thereof.

5. The pharmaceutical composition according to claim 1, wherein at least the progesterone is in suspension in the oil.

6. The pharmaceutical composition according to claim 1, in the form of a soft capsule.

7. The pharmaceutical composition according to claim 1, in unit dosage form comprising between 2 mg and 600 mg of micronized progesterone.

8. A method for preparing a pharmaceutical composition comprising the following successive steps:
   mixing olive oil with soy bean lecithin in order to obtain a mixture; and
   adding micronized progesterone to said mixture to obtain a homogeneous suspension, wherein at least about 80% of the particles of said micronized progesterone are characterized by a particle size of between 1 and 15 µm, as measured in the composition.

9. A method for the treatment of a physiological condition linked to insufficiency of progesterone secretion comprising the step of administering to the patient a pharmaceutical composition comprising: micronized progesterone, soy bean lecithin, and olive oil, wherein at least about 80% of the particles of said micronized progesterone are characterized by a particle size of between 1 and 15 µm, as measured in the composition.

10. The method according to claim 9, in which the pharmaceutical composition further contains an oestrogen, or an ester-type derivative thereof.

11. The pharmaceutical composition according to claim 1, wherein the progesterone/oil ratio is between 0.25/1 and 2/1.

12. The pharmaceutical composition according to claim 1, wherein the progesterone/oil ratio is between 0.40/1 and 1/1.

13. The pharmaceutical composition according to claim 1, wherein the progesterone/oil ratio is 0.67/1.

14. The pharmaceutical composition according to claim 1, wherein the soy bean lecithin/oil ratio is between 0.01/1 and 0.2/1.

15. The pharmaceutical composition according to claim 1, wherein the soy bean lecithin/oil ratio is between 0.040/1 and 0.1/1.

16. The pharmaceutical composition according to claim 1, wherein the soy bean lecithin/oil ratio is 0.0067/1.

17. The pharmaceutical composition according to claim 4, wherein the oestrogen, or the ester-type derivative thereof is selected from the group consisting of 17-beta-oestradiol, oestrone, 17-alpha-ethinyl oestradiol and oestradiol valerianate, or phyto-oestrogens.

18. The pharmaceutical composition according to claim 4, wherein the oestrogen, or the ester-type derivative thereof is 17-beta-oestradiol.

19. The pharmaceutical composition according to claim 7, comprising between 30 mg and 300 mg of micronized progesterone.

20. The pharmaceutical composition according to claim 7, comprising between 100 mg and 200 mg of micronized progesterone.

21. The pharmaceutical composition according to claim 1, wherein at least 50% of the particles of said micronized progesterone have a particle size of between 1 and 10 µm, as measured in the composition.

22. The pharmaceutical composition according to claim 1, wherein at least 25% of the particles of said micronized progesterone have a particle size of between 1 and 5 µm, as measured in the composition.

23. The method according to claim 10, wherein the oestrogen, or the ester-type derivative thereof is selected from the group consisting of 17-beta-oestradiol, oestrone, 17-alpha-ethinyl oestradiol and oestradiol valerianate, or phyto-oestrogens.

24. The method according to claim 10, wherein the oestrogen, or the ester-type derivative thereof is 17-beta-oestradiol.

25. The method according to claim 9, wherein at least 50% of the particles of said micronized progesterone have a particle size of between 1 and 10 µm, as measured in the composition.

26. The method according to claim 9, wherein at least 25% of the particles of said micronized progesterone have a particle size of between 1 and 5 µm, as measured in the composition.

* * * * *